(12) United States Patent
Komatsubara

(10) Patent No.: US 9,456,886 B2
(45) Date of Patent: Oct. 4, 2016

(54) ABSORBENT ARTICLE FOR PET ANIMALS

(71) Applicant: UNICHARM CORPORATION, Shikokuchuo-shi, Ehime (JP)

(72) Inventor: Daisuke Komatsubara, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/387,815

(22) PCT Filed: Jun. 16, 2014

(86) PCT No.: PCT/JP2014/065951
§ 371 (c)(1),
(2) Date: Sep. 24, 2014

(87) PCT Pub. No.: WO2015/005069
PCT Pub. Date: Jan. 15, 2015

(65) Prior Publication Data
US 2015/0272713 A1    Oct. 1, 2015

(30) Foreign Application Priority Data
Jun. 6, 2014 (JP) .................... 2014-118172

(51) Int. Cl.
| A61F 13/15 | (2006.01) |
| A61F 13/20 | (2006.01) |
| A61D 99/00 | (2006.01) |
| A01K 23/00 | (2006.01) |
| A61F 13/49 | (2006.01) |
| A61F 13/56 | (2006.01) |

(52) U.S. Cl.
CPC .............. *A61D 99/00* (2013.01); *A01K 23/00* (2013.01); *A61F 13/49014* (2013.01); *A61F 13/49019* (2013.01); *A61F 13/5638* (2013.01); *A61F 2013/15186* (2013.01)

(58) Field of Classification Search
CPC ................ A01K 23/00; A61F 13/15; A61F 2013/15186
USPC ................ 604/385.01, 385.09; 119/169
See application file for complete search history.

(56) References Cited

U.S. PATENT DOCUMENTS

| 7,195,618 B2 * | 3/2007 | Ikegami | ............... A01K 23/00 604/345 |
| 8,020,523 B2 * | 9/2011 | Ikegami | ............... A01K 23/00 119/869 |

(Continued)

FOREIGN PATENT DOCUMENTS

| JP | 2004-159591 A | 6/2004 |
| JP | 2007-167007 A | 7/2007 |

(Continued)

OTHER PUBLICATIONS

International Search Report mailed Jul. 8, 2014 in International Application No. PCT/JP2014/065951 filed Jun. 16, 2014.

*Primary Examiner* — Michele M Kidwell
(74) *Attorney, Agent, or Firm* — Hauptman Ham, LLP

(57) ABSTRACT

An absorbent article having a longitudinal direction and a transverse direction orthogonal to the longitudinal direction includes an absorbent panel having a ventral region, a dorsal region and an intermediate region between the ventral and dorsal regions in the longitudinal direction. The absorbent panel includes a liquid-permeable topsheet, a liquid-impermeable backsheet and a liquid absorbent core lying between the liquid-permeable topsheet and the liquid-impermeable backsheet. The absorbent core is arranged in a limited area extending from a zone of the intermediate region defined adjacent to a slit for formation of an opening into which the pet animal's tail is inserted into the ventral region and has a first end lying in the ventral region and a second end lying in the intermediate region. A dimension of the ventral region in the transverse direction gradually narrows from the side of the second end toward the first end.

7 Claims, 14 Drawing Sheets

(56) References Cited

U.S. PATENT DOCUMENTS

2005/0154367 A1* 7/2005 Ikegami .............. A01K 23/00
 604/389
2007/0149941 A1 6/2007 Ikegami et al.

FOREIGN PATENT DOCUMENTS

| JP | 2013-000034 A | 1/2013 |
|----|---------------|--------|
| WO | 2012-172806 A | 12/2012 |

* cited by examiner

FIG.4
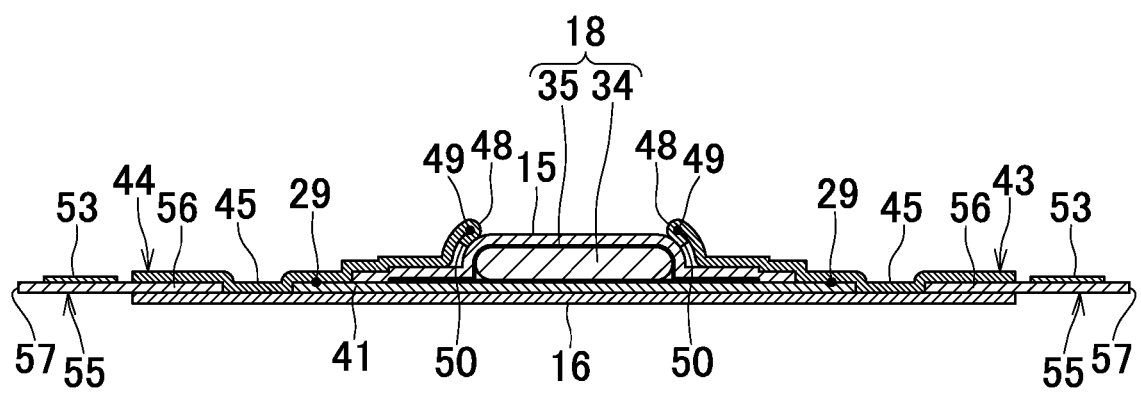
FIG.5
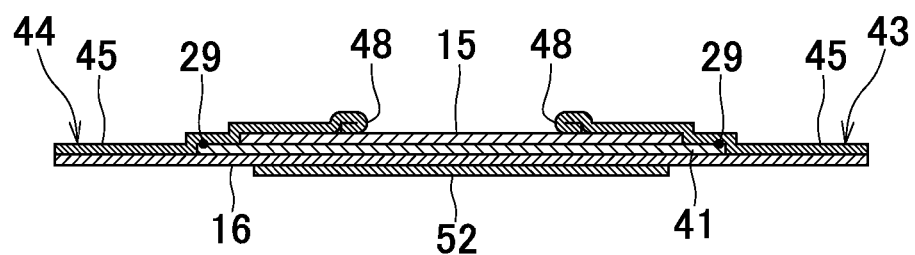
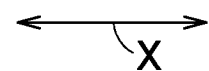

FIG.13
(a)
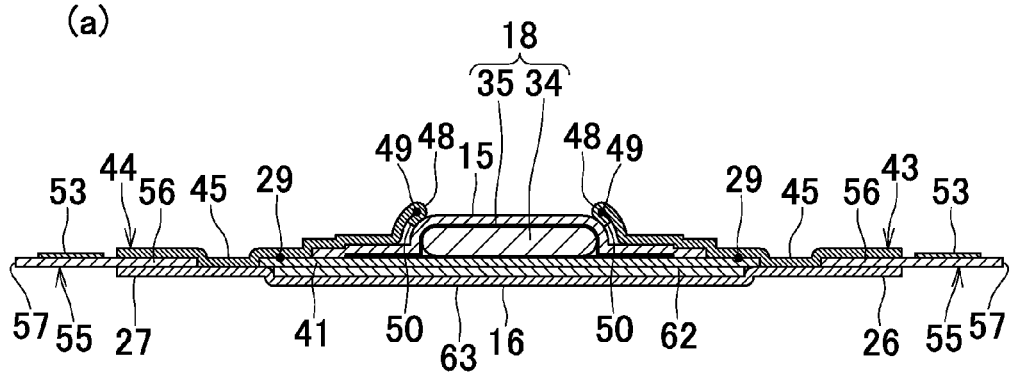
(b)
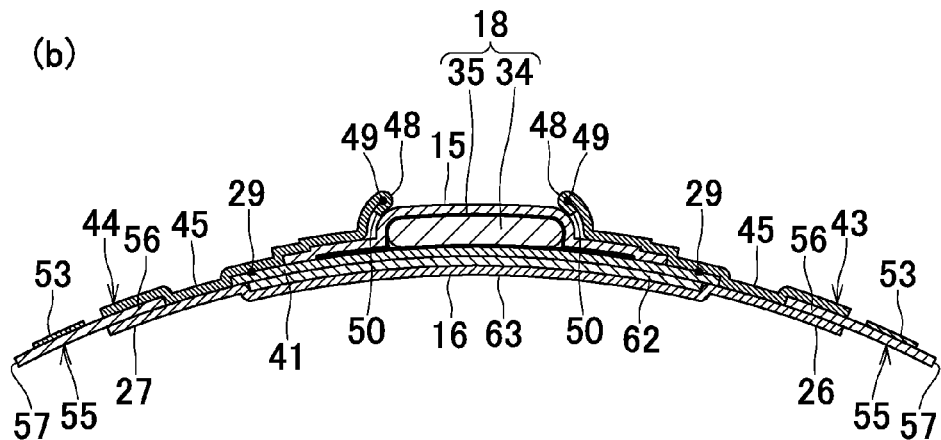

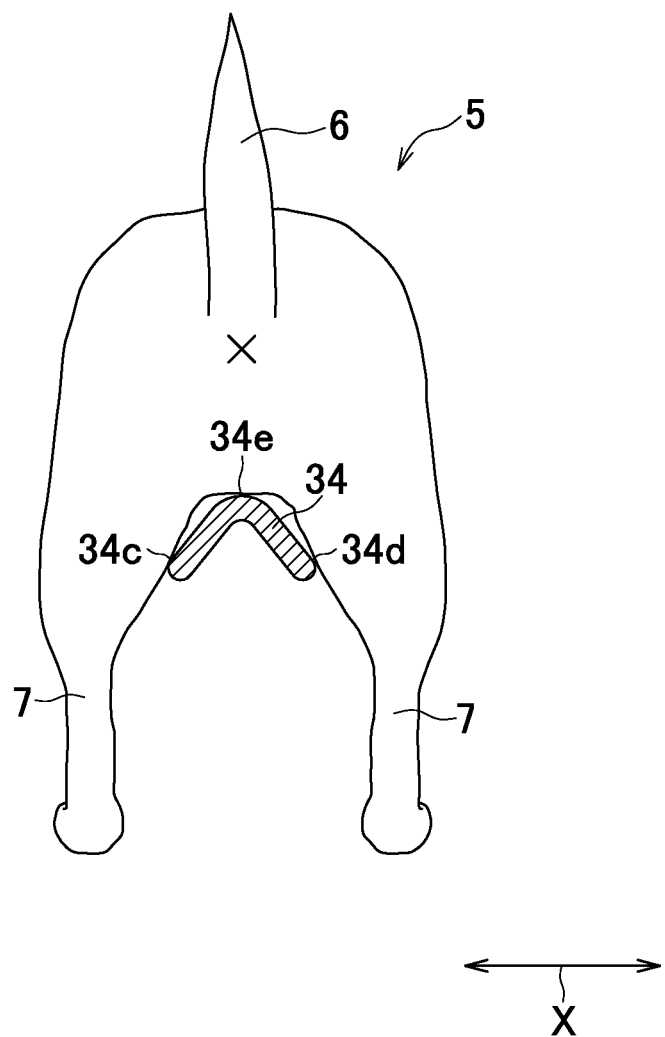

ABSORBENT ARTICLE FOR PET ANIMALS

RELATED APPLICATIONS

The present application is a National Phase of International Application Number PCT/JP2014/065951, filed Jun. 16, 2014, which claims priority to Japanese Application No. 2014-118172, filed Jun. 6, 2014.

TECHNICAL FIELD

The present invention relates to absorbent articles of pet animals, for example, dogs.

BACKGROUND

Conventionally, absorbent articles for pet animals are known having a longitudinal direction, a transverse direction being orthogonal thereto, a body-contact surface facing the pet animal's body and a non-body-contact surface lying on the opposite side thereof, and including a ventral region, a dorsal region, an intermediate region defined between the ventral region and the dorsal region, a liquid-permeable interior sheet, a liquid-impermeable exterior sheet and a liquid absorbent core lying between the interior sheet and the exterior sheet.

For example, Patent Literature 1 discloses an absorbent article having a topsheet as the interior sheet, a backsheet as the exterior sheet and a liquid absorbent core lying between the interior and the exterior sheets. In this absorbent article, the liquid absorbent core has a generally rectangular shape and has a first end lying in the ventral region and a second end lying in the intermediate region wherein the width of the liquid absorbent core is uniform all thereover.

CITATION LIST

Patent Literature

{PTL 1}: JP 2004-159591 A

SUMMARY

Technical Problem

In the absorbent article disclosed in PTL 1, the width of the absorbent core is uniform all thereover. In consequence, the liquid absorbent core is apt to be indirectly caught by both rear legs of the pet animal when it is tried to pass the first end of the liquid absorbent core between both rear legs of the pet animal to put the absorbent article on the pet animal's body. For this reason, this known absorbent article has a problem such that a handling to put the article on the pet animal's body is difficult or, at least, it is not easy to pass the liquid absorbent core between the pet's both rear legs.

An object of the present invention is to provide an absorbent article for pet animal improved so as to restrict the possibility that the liquid absorbent core might be indirectly caught by the rear legs when it is tried to pass the portion between both the rear legs of the pet animal, thereby facilitating the article to be put on the pet animal's body.

Solution to Problem

The present invention relates to an absorbent article for pet animal having a longitudinal direction, a transverse direction being orthogonal thereto, a body-contact surface facing pet animal's body and a non-body-contact surface lying on the side opposite thereto and including an absorbent panel having a ventral region, a dorsal region and an intermediate region defined between the ventral region and the dorsal region as viewed in the longitudinal direction wherein the absorbent panel includes a liquid-permeable interior sheet, a liquid-impermeable exterior sheet and a liquid absorbent core lying between these interior and exterior sheets.

The liquid absorbent core in the present invention is arranged in a limited area extending from a zone of the intermediate region defined adjacent to a slit for formation of an opening into which the pet animal's tail is inserted into the ventral region and has a first end lying in the ventral region and a second end lying in the intermediate region opposed to each other in the longitudinal direction; and a dimension in the transverse direction of the ventral region of the liquid absorbent core gradually narrows from the side of the second end toward the first end.

Advantageous Effects of Invention

In one or more embodiments of the absorbent article for pet animal according to the present invention, a dimension in the transverse direction of the ventral region of the liquid absorbent core gradually decreases from the second end side toward the first end side and consequentially it is possible to restrict a possibility that the liquid absorbent core might be indirectly caught by the rear legs of the pet animal in the course of guiding the liquid absorbent core between the both rear legs of the pet animal so that the absorbent article may be easily put on the body of the pet animal.

BRIEF DESCRIPTION OF DRAWINGS

The drawings illustrate specific embodiments of the present invention including optional and preferred embodiments as well as essential features of the invention.

FIG. 4 is a schematic sectional view taken along line IV-IV in FIG. 2.

FIG. 5 is a schematic sectional view taken along line V-V in FIG. 2.

FIG. 13 (*a*) is a view similar to FIG. 4, illustrating the diaper according to the second embodiment and FIG. 13 (*b*) is a sectional view illustrating a state in which a central region in a transverse direction of the ventral region protrudes toward the side of a body-contact surface with respect to both side edges under contraction of ventral side elastic members.

FIG. 16 is an explanatory diagram illustrating a relationship between the pet animal and the first end portion with the diaper put on the pet animal's body.

DESCRIPTION OF EMBODIMENTS

Figure 1:
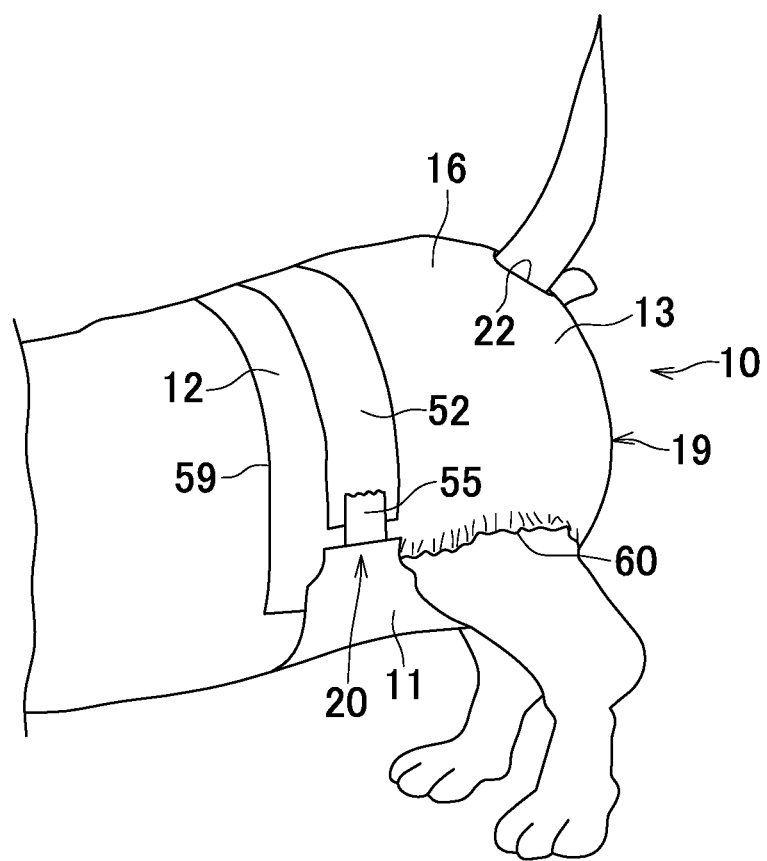
FIG. 1 is a perspective view illustrating a diaper according to a first embodiment as an example of an absorbent article for pet animals according to the present invention put on a dog's body.

The embodiments described below relate to an absorbent article for pet animals as illustrated in FIGS. 1-16, including both optional and preferred features as well as those features which are essential features of the present invention.

First Embodiment

FIGS. 1 through 9 illustrate a first embodiment of a diaper 1 according to the present invention. In this regard, FIGS. 2 through 6 illustrate a state in which elastic members 29, 49 described hereunder in more details are stretched (i.e., a state under tension). The diaper 10 has a longitudinal direction Y, a transverse direction X being orthogonal thereto, a pet animal's body-contact surface and a non-body-contact surface opposite thereto, a longitudinal center line P bisecting a dimension in the transverse direction X and extending in the longitudinal direction Y and a transverse center line Q bisecting a dimension in the longitudinal direction X and extending in the transverse direction X. The diaper 10 includes, a ventral region 11, a dorsal region 12, an intermediate region 13 lying between the ventral region 11 and the dorsal region 12, a topsheet (interior sheet) 15, a backsheet (exterior sheet) 16, an absorbent panel 19 having an absorbent structure 18 having an absorbent core 34 disposed between the topsheet 15 and the backsheet 16 so as to extend at least in the intermediate region 13 and fasteners 20 to fasten the ventral region 11 and the dorsal region 12 to each other. With the diaper 10 put on the pet animal such as dog, the ventral region 11 faces the belly of the pet animal, the dorsal region 12 faces the back of the pet animal and the intermediate region 11 faces the buttocks of the pet animal.

Figure 2:
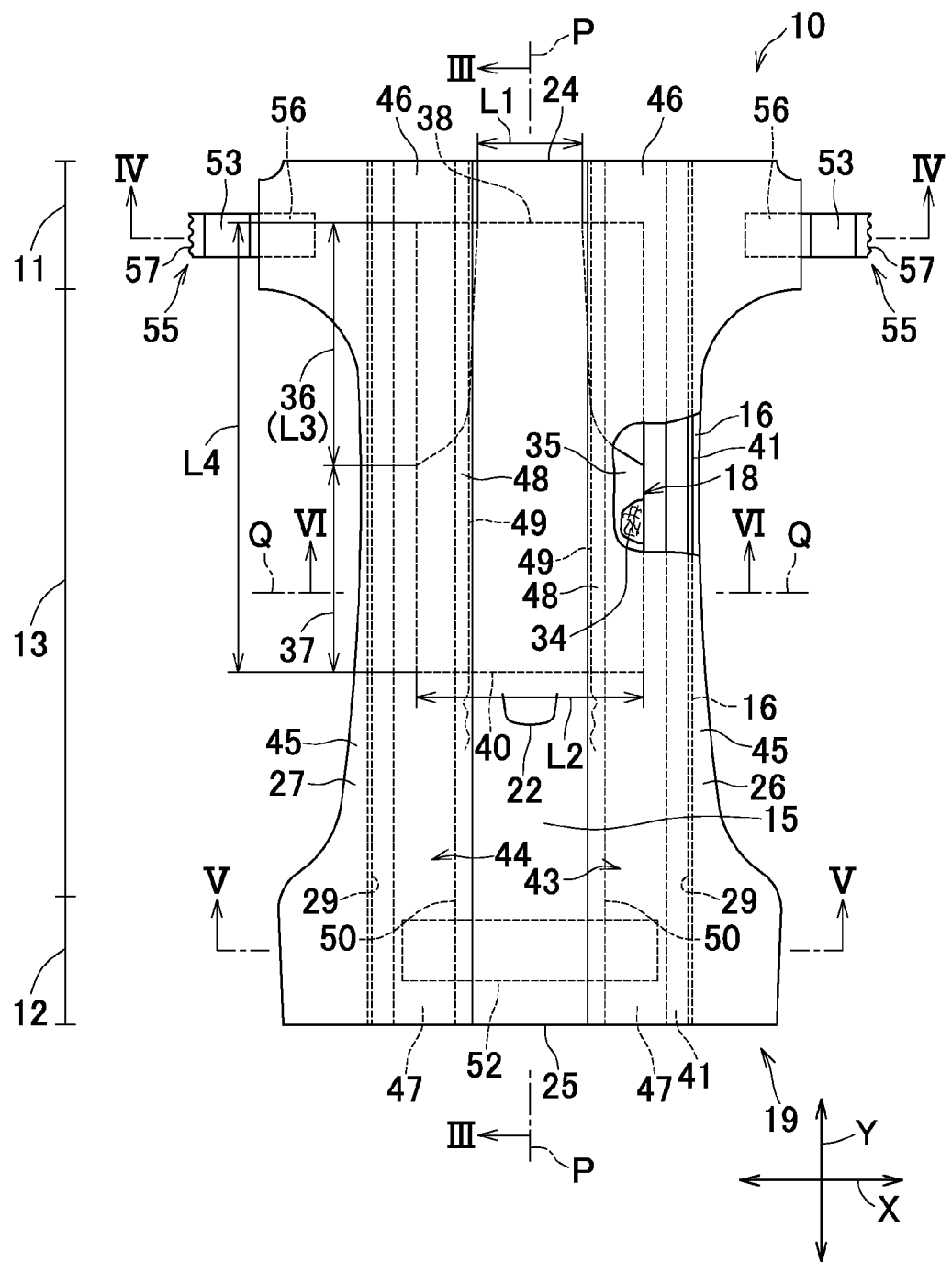
FIG. 2 is a plan view of the diaper.
Figure 3:
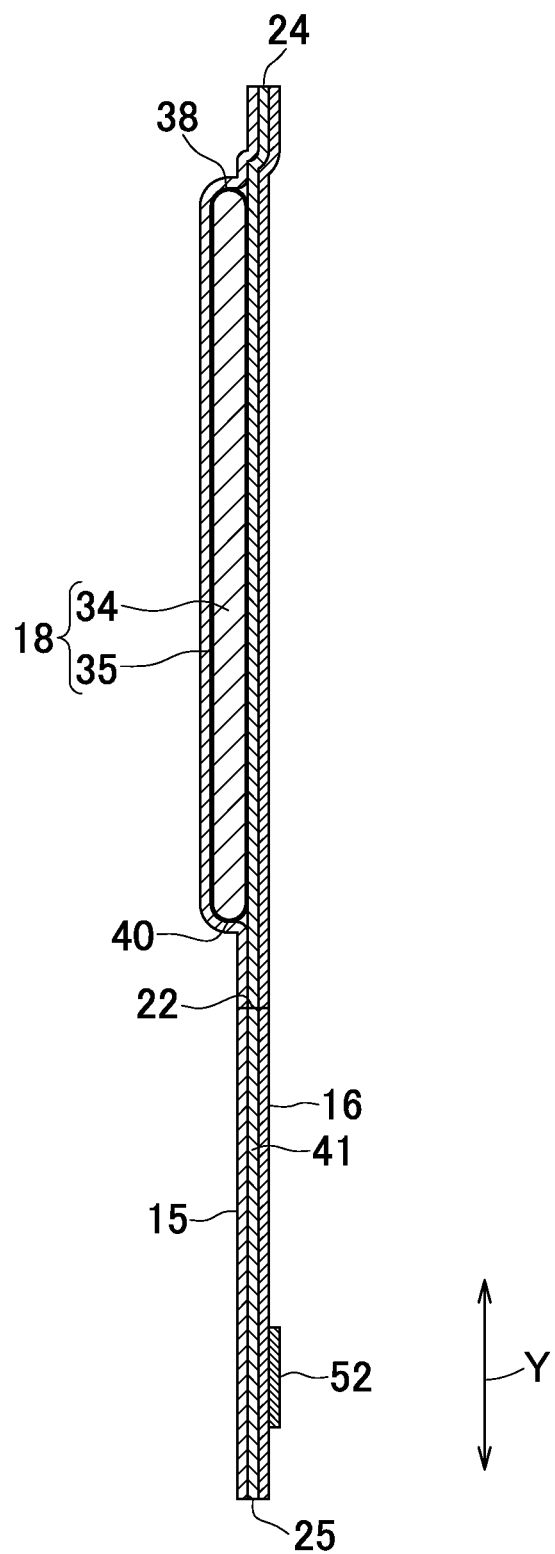
FIG. 3 is a schematic sectional view taken along line III-III in FIG. 2.

Referring to FIG. 2, the absorbent panel 19 includes the topsheet 15, the backsheet 16 and the absorbent body 18 interleaved between the topsheet 15 and the backsheet 16. Referring to FIGS. 2 through 6, the absorbent panel 19 includes a first end 24 and a second end 25 opposed to each other in the longitudinal direction Y and both extending in the transverse direction X and both lateral portions 26, 27 opposed to each other in the transverse direction X and extending in the longitudinal direction Y.

The topsheet 15 may be formed of fibrous nonwoven fabric, a porous plastic film or a laminate thereof. For example, the topsheet may be formed of an air-through fibrous nonwoven fabric, a spunbond fibrous nonwoven fabric or a pointbond fibrous nonwoven fabric. These nonwoven fabrics have for example, amass of about 10 g/m2 40 g/m2.

The backsheet 16 lies on the exterior surface of the absorbent panel 19 and may be formed of material such as a moisture-permeable plastic film, a fibrous nonwoven fabric or a laminate sheet thereof. For example, the backsheet 16 may be formed of a spunbond fibrous nonwoven fabric having a mass per unit area in a range of 8 to 30 g/m2.

Figure 6:
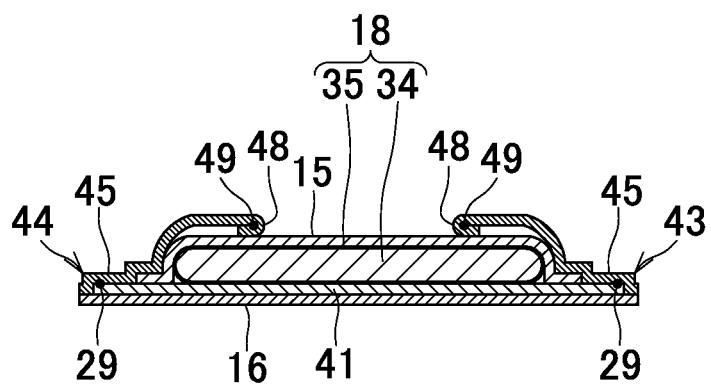
FIG. 6 is a schematic sectional view taken along line VI-VI in FIG. 2.

The topsheet 15 and the backsheet 16 extend outward beyond a peripheral edge of the absorbent body 18 and are joined to each other in the respective regions of these two sheets 15, 16 extending outward in this manner with, for example, hot melt adhesive (not shown) distributed on at least one of the opposed surface of these two sheets 15, 16. A leakage-barrier sheet 41 may be interposed between these two sheets 15, 16 and the absorbent body 18 may be secured on the leakage-barrier sheet 41. In the intermediate region 13 of the absorbent panel 19, the sheets 15, 16 and the leakage-barrier sheet 41 are disposed with a slit 22 for formation of an opening through which the pet animal's tail may be exposed outward. Referring to FIGS. 4 through 6, for example, a dimension in the transverse direction X of the topsheet 15 may be smaller than a dimension in the transverse direction X of the leakage-barrier sheet 41.

Unlike well-known disposable diapers for the human being, in the ventral region 11 and the dorsal region 12 of the diaper 10, none of elastic members extending in the transverse direction X is arranged. In this way, it is possible to restrict a situation occurring particularly in the dorsal region 12 such that the sheets 15, 16 might contract in the transverse direction X if such elastic members extending in the transverse direction X are arranged in this region 12 and whereby it is possible to restrict contraction in the transverse direction X of a first fastening element 52 formed from a group of loops of a mechanical fastener as described later. Consequently, it is assured that the first fastening element 52 and a pair of second fastening elements 53 are easily fastened to each other.

The absorbent structure 18 includes the absorbent core 34 formed, for example, from a mixture of wood fluff pulp and absorbent polymer particles and a liquid-diffusive sheet 35, for example, tissue paper to wrap the absorbent core 34. The absorbent structure 18 is arranged in a limited area extending in the longitudinal direction Y from the intermediate region 13 to the ventral region 11, more specifically, extending from a zone of the intermediate region 13 defined adjacent to the slit 22 into the ventral region 11.

The absorbent core 34 has a first end 38 in the ventral region 11 and a second end 40 in the intermediate region 13 and these ends 38, 40 are opposed to each other in the longitudinal direction Y wherein the absorbent core 34 is divided into a narrow region 36 having the first end 38 and a wide region 37 having the second end 40. In the wide region 37, a dimension in the transverse direction X of the absorbent core 34 is uniform. In the absorbent core 34, a dimension L1 in the transverse direction X measured along the first end 38 is smaller than a dimension L2 in the transverse direction X measured along the second end 40 and, in the narrow region 36, the width thereof gradually shrinks from the side of the second end 40 toward the first end 38. In a state free from any effect of the contractile strength of elastic members 29, 49 (described later), a dimension L3 in the longitudinal direction Y of the narrow region 36 of the absorbent core 34 is preferably in a range of about 30 to about 90% of a dimension L4 in the longitudinal direction Y of the absorbent core 34. The dimension L1 in the transverse direction X of the core 34 measured along the first end 38 may be, for example, in a range of about 50 to about 80 mm. The dimension L1 in the transverse direction X of the core 34 measured along the first end 38 is in a range of about 30 to 70% of the dimension L2 in the transverse direction X measured along the second end 40. The term "the first end 38" used herein means the most distal portion on one side of the absorbent core 34. The term "the side of the second end 40" used herein means the most distal portion on the other side of the absorbent core 34 including the vicinity thereof.

Referring to FIGS. 3 through 6, the leakage-barrier sheet 41 form of a liquid-impermeable but moisture-permeable plastic film is arranged between the topsheet 15 and the backsheet 16. The leakage-barrier sheet 41 is secured by the intermediary of, for example, hot melt adhesive (not shown) distributed to one of the opposed surfaces of the sheets 15, 16.

Referring to FIGS. 2 through 6, the absorbent panel 19 further includes a pair of containment sheets 43, 44 extending in the longitudinal direction Y on the body-contact surface of the topsheet 15. The containment sheets 43, 44 are arranged symmetrically about the longitudinal center line P. The containment sheets 43, 44 partially define the both lateral portions 26, 27 and include proximal portions 45 secured to the body-contact surface of the topsheet 15, front and rear end portions 46, 47 defined by respective pair of end portions opposed in the longitudinal direction Y and secured to the body-contact surface of the topsheet, and distal portions 48 extending in the longitudinal direction Y and formed by inner side edge portions 50 of the respective containment sheets 43, 44 folded back inward.

Lateral elastic members 29 extending in the longitudinal direction Y are attached between the containment sheets 43, 44 and the backsheet 16, more specifically, between the containment sheets 43, 44 and the leakage-barrier sheet 41. As the lateral elastic members 29, strand- or string-like elastic members having a fineness in a range of about 200 to 1000 dtex may be used. The lateral elastic members 29 are contractibly attached under tension in the longitudinal direction Y in in the ventral region 11, the intermediate region 13 and the dorsal region 12.

The respective distal portions 48 of the containment sheets 43, 44 are disposed with strand- or string-like containment elastic members 49 contractibly attached under tension in the longitudinal direction Y. Referring to FIG. 2, respective zones of the containment sheets 43, 44 in which the absorbent structure 18 is present as viewed in the transverse direction X are disposed with the containment elastic members 49 attached thereto under tension. In contrast, respective zones of the intermediate region 13 defined in the vicinity of the dorsal region 12, in which the absorbent structure 18 is not present as viewed in the transverse direction X, are disposed with the containment elastic members 49 attached in a relaxed state to the containment sheets 43, 44 in a relaxed state to the containment sheets 43, 44, in other words, without a possibility that the containment sheets 43, 44 might be affected by any contractile force. Consequently, as illustrated in FIG. 7, with the first and second fastening elements 52, 53 fastened to each other and whereby the ventral region 11 joined to the dorsal region 12, the distal portions 48 are pulled off from the body-contact surface of the topsheet 15 under contraction of the containment elastic members 49 in the respective zones in which the absorbent structure 18 is present as viewed in the longitudinal direction Y and whereby the containment sheets 43, 44 form a pair of barriers functioning to prevent body waste from leaking sideways.

The fastener 20 includes the first fastening element 52 formed of a group of loops for a mechanical fastener extending in the transverse direction X (see FIGS. 1 and 2) and the second fastening element 53 formed of a group of hooks for the mechanical fastener adapted to be fastened to the first fastening element 52. Respective proximal portions 56 of a pair of fastening tabs 55 lie between the containment sheets 43, 44 and the backsheet 16 and these proximal portions 56 are secured, for example, with hot melt adhesive (not shown) distributed to the sheets 43, 44. Each of the fastening tabs 55 is preferably formed of sheet material having relatively high stiffness and tensile strength, for example, a plastic film, a fibrous nonwoven fabric, a laminate thereof or a craft paper. The second fastening elements 53 are attached to respective distal portions 57 in a pair of the fastening tabs 55 distanced from each other symmetrically about the longitudinal center line P.

Figure 8:
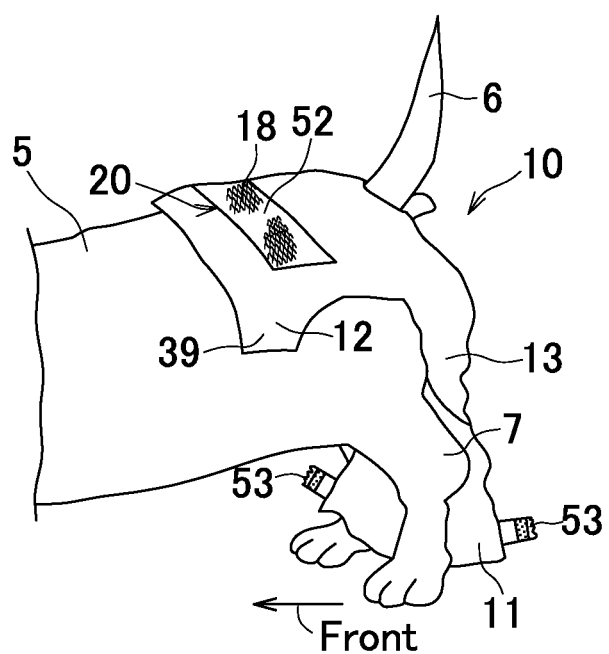
FIG. 8 is a perspective view illustrating a process of putting the diaper on the body of the pet animal.
Figure 9:
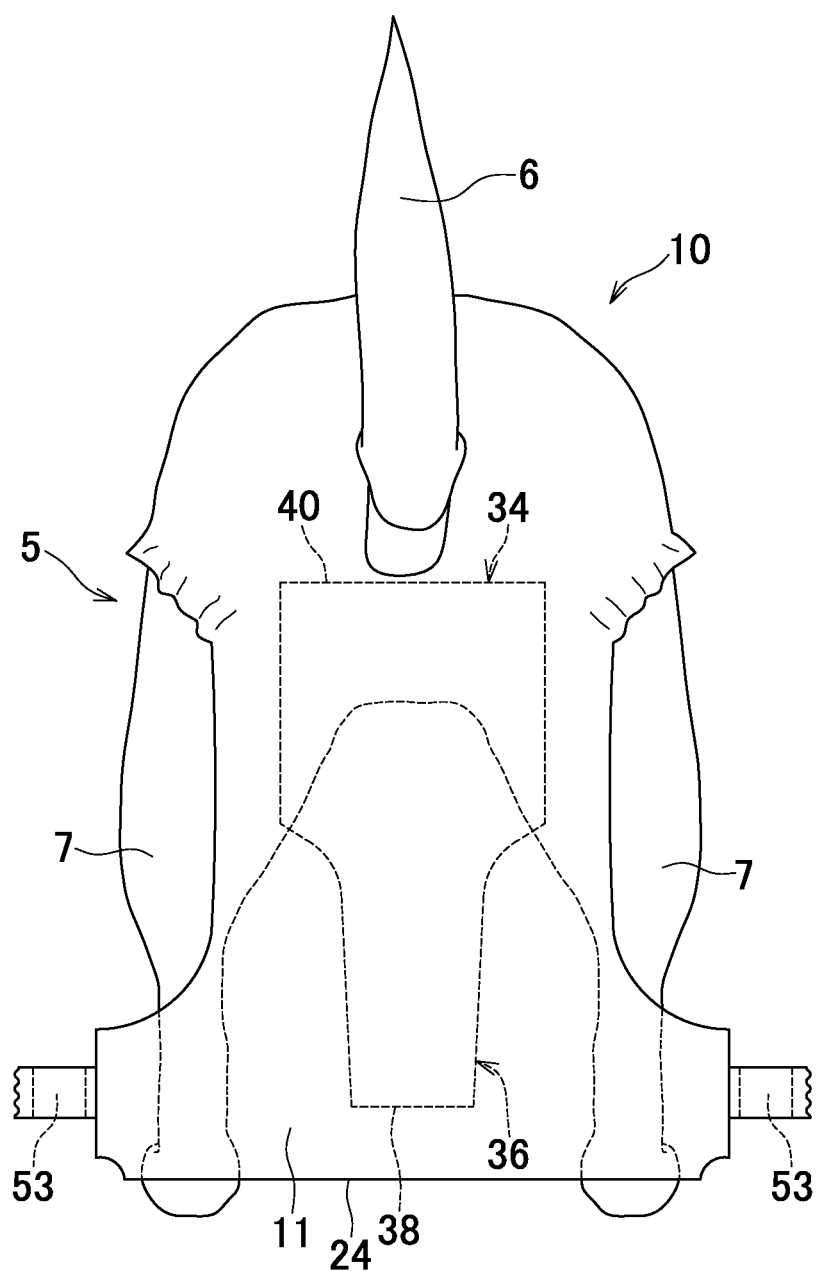
FIG. 9 is a perspective view illustrating, from behind, a process of putting the diaper on the body of the pet animal.
Figure 10:
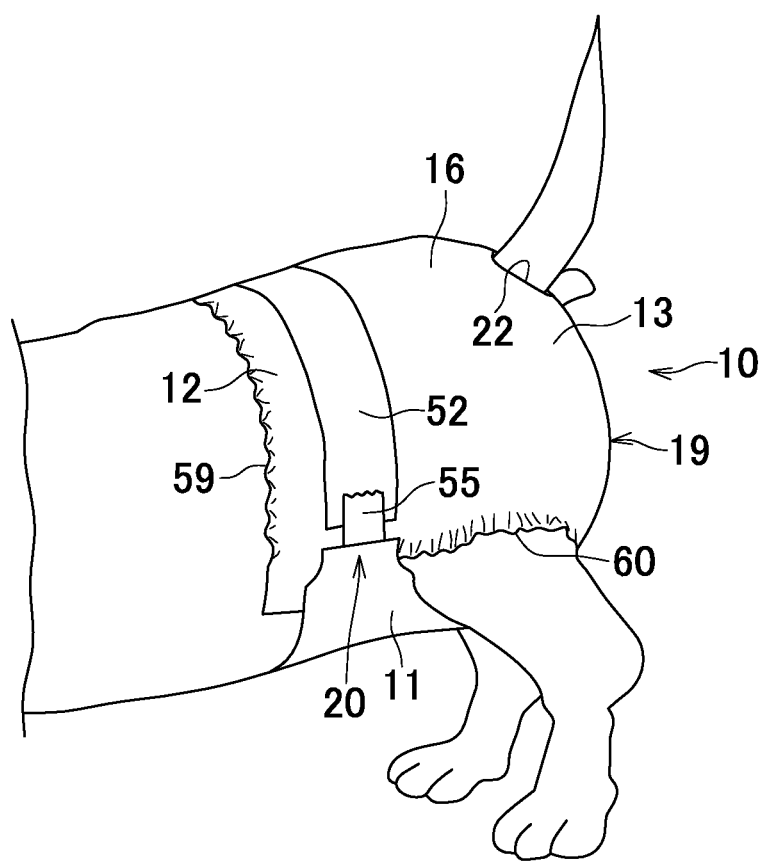
FIG. 10 is a view similar to FIG. 1, illustrating the diaper according to a second embodiment.

Referring to FIG. 8, in the course of putting the diaper 10 on a pet animal 5, first, the slit 22 is forced to form an opening into which a tail 6 of the pet animal is inserted and the back of the pet animal 5 is put in contact with the dorsal region 12. In this state, as illustrated in FIG. 9, the narrow region 36 of the absorbent core 34 lies between both rear legs of the pet animal 5. In this step, the ventral region 11 defines the lower end of the diaper 10 and the second fastening elements 53 lie on both outer sides in the transverse direction X of the ventral region 11. In this state, the ventral region 11 in which the absorbent core 34 is present may be pinched with fingers to let the first end 24 of the absorbent panel 19 pass between the both rear legs 7 of the pet animal 5. For the reason that the dimension in the transverse direction X of the absorbent core 34 in the ventral region 11 gradually narrows from the side of the second end 40 toward the first end 38, it is possible to restrict a possibility that the first end 38 of the absorbent core 34 might be indirectly caught by the both rear legs 7 in this step, thereby facilitating the diaper 10 to be put on the pet animal 5.

Figure 7:
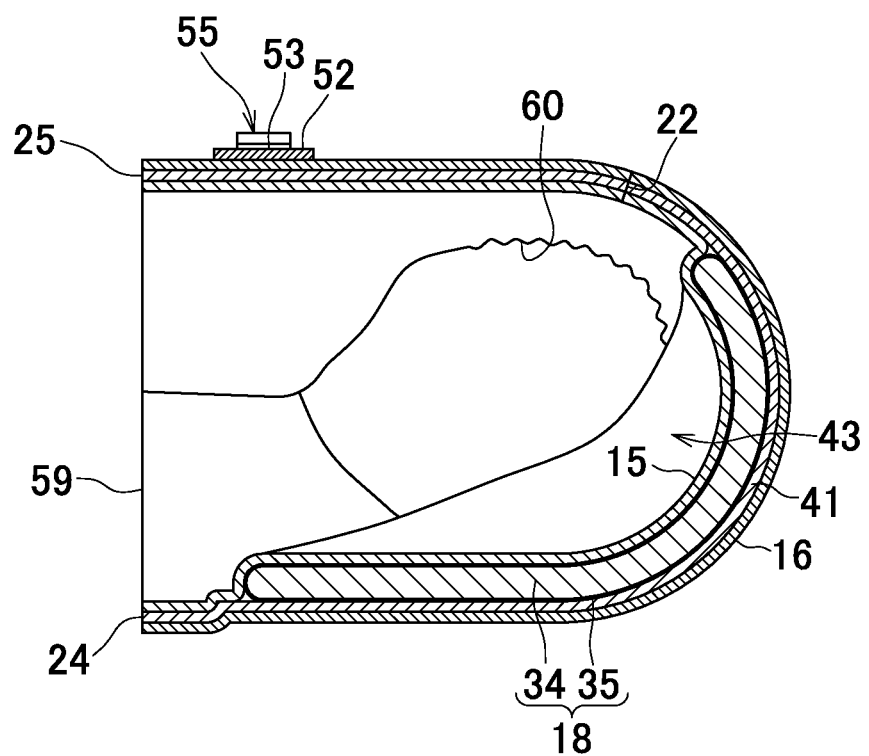
FIG. 7 is a schematic sectional view of the diaper having a ventral region and a dorsal region fastened with each other by means of first and second fastening elements.

Thereafter, the first fastening element 52 and the second fastening elements 53 may be fastened to each other to define a waist-opening 59 and a pair of rear leg-openings 60 (see FIGS. 1 and 7). The waist-opening 59 is defined by the first end 24 of the ventral region 11 of the absorbent panel 19 and the second end 25 of the dorsal region 12 and the rear leg-openings 60 are defined by the both lateral portions 26, 27. In this regard, while the fastening tabs 55 are exemplarily illustrated to be attached with, for example, hot melt adhesive distributed to the backsheet 16, it is also possible to arrange the topsheet so as to extend in the transverse direction beyond the periphery of the backsheet and to attach the fastening tabs to these projecting portions of the topsheet with, for example, hot melt adhesive distributed to these projecting portions of the topsheet.

According to this diaper 10, in addition to the functions and the effects as described hereinabove, the respective proximal portions 45 of the containment sheets 43, 44 are not in overlapping relationship with the absorbent core 34 and the respective front and rear end portions 46, 47 of the containment sheets 43, 44 are also not in overlapping relationship with the absorbent core 34. Consequently, it is possible to restrict a possibility that the stiffness of the absorbent core might decrease the contractile force of the containment elastic members 49. Restricting the undesirable influence of stiffness of the absorbent core 34, it is possible to assure that the containment sheets 43 raise themselves on the absorbent structure 18 under the contractile force of the containment elastic members 49. In this way, it is possible to prevent body fluids such as urine from leaking beyond the both lateral portions 26, 27 of the diaper 10 in the transverse direction X.

Furthermore, the first end 38 of the absorbent core 34 partially extends outward in the longitudinal direction Y beyond the respective ends of the proximal portions 56 on the side of the dorsal region 12 so that, when the first end 24 of the absorbent panel 19 is passed between the both rear legs 7 of the pet animal 5, the portion to be passed between the both rear legs 7 includes therein the absorbent core 34 having relatively high stiffness. For this reason, shape retention of the absorbent core 34 is sufficiently assured to facilitate the first end 24 to be passed between the both rear legs 7 of the pet animal 5. Additionally, the absorbent core 34 is continuous in the longitudinal direction Y from the ventral region 11 toward the intermediate region 13 and therefore it is easy to pinch the portion in which the high stiffness absorbent core 34 is present.

Second Embodiment

FIGS. 10 through 16 illustrate the diaper 10 according to a second embodiment. On the side of the first end 24 of the ventral region 11 in this diaper 10, a ventral side elastic member 62 extending in the transverse direction X is attached between the absorbent structure 18 and the backsheet 16, more specifically, between the leakage-barrier sheet 41 and the backsheet 16. The ventral side elastic member 62 is formed of, for example, an elastomer resin such as polyurethane in a belt-like shape.

In a state free from contractile force of the elastic members 29, 49, 62, the narrow region 36 of the absorbent core 34 gradually narrows from the first end 38 of the ventral region 11 toward the transverse central line Q and then gradually widens again as being closer to the transverse central line Q. In the wide region 37 of the absorbent core 34, the dimension thereof in the transverse direction X is constant as long as the core 34 is free from the contractile force of the elastic members 29, 49, 62.

Figure 11:
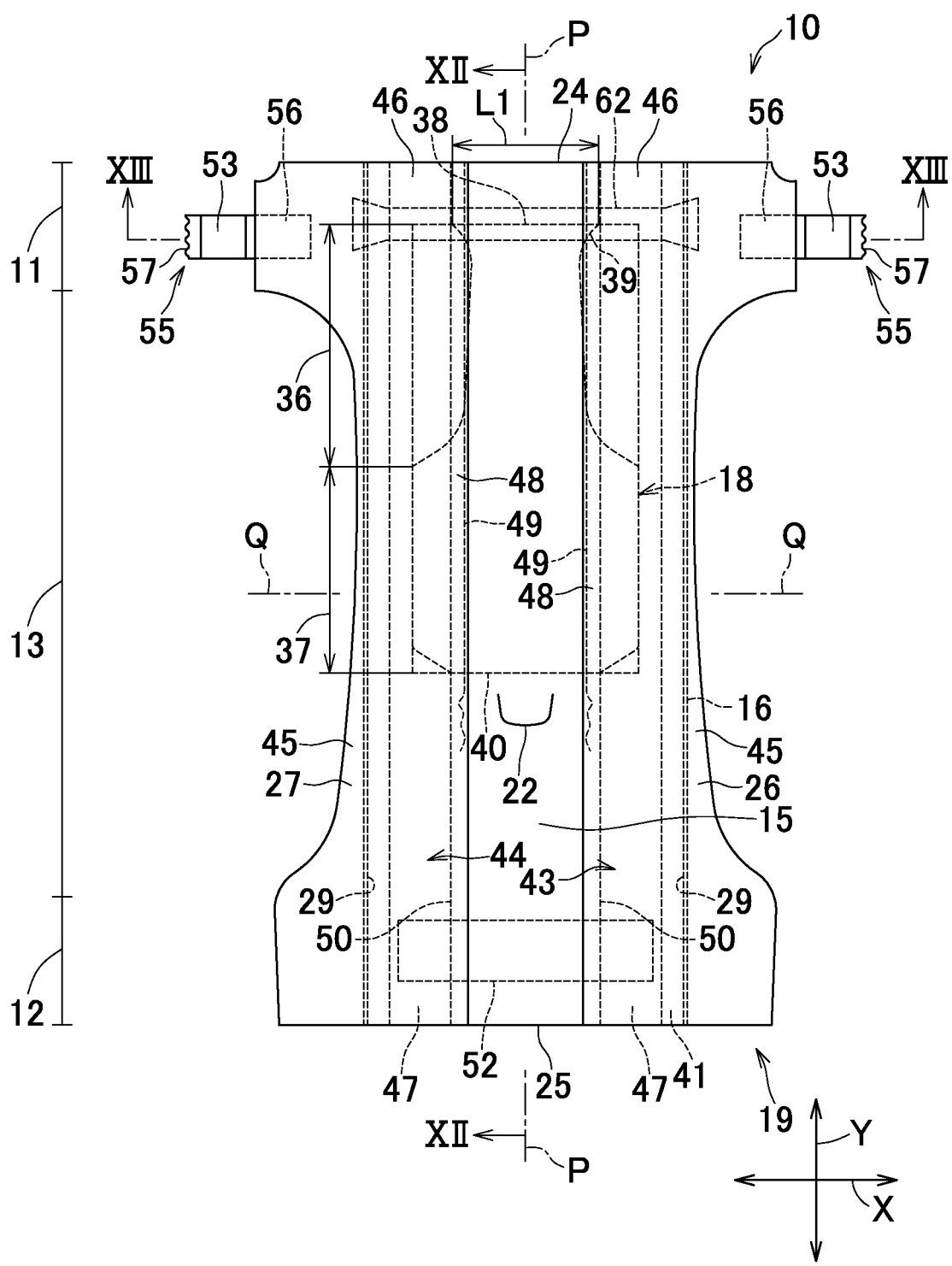
FIG. 11 is a view similar to FIG. 2, illustrating the diaper according to the second embodiment.
Figure 12:
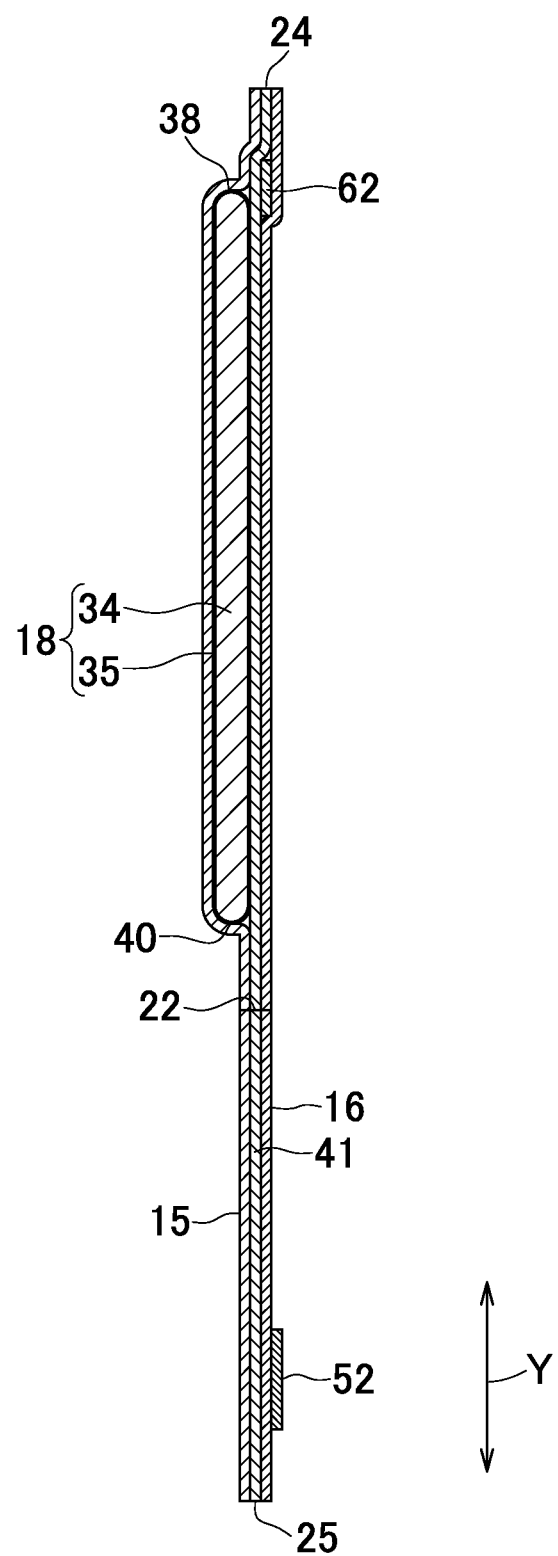
FIG. 12 is a view similar to FIG. 3, illustrating the diaper according to the second embodiment.
Figure 14:
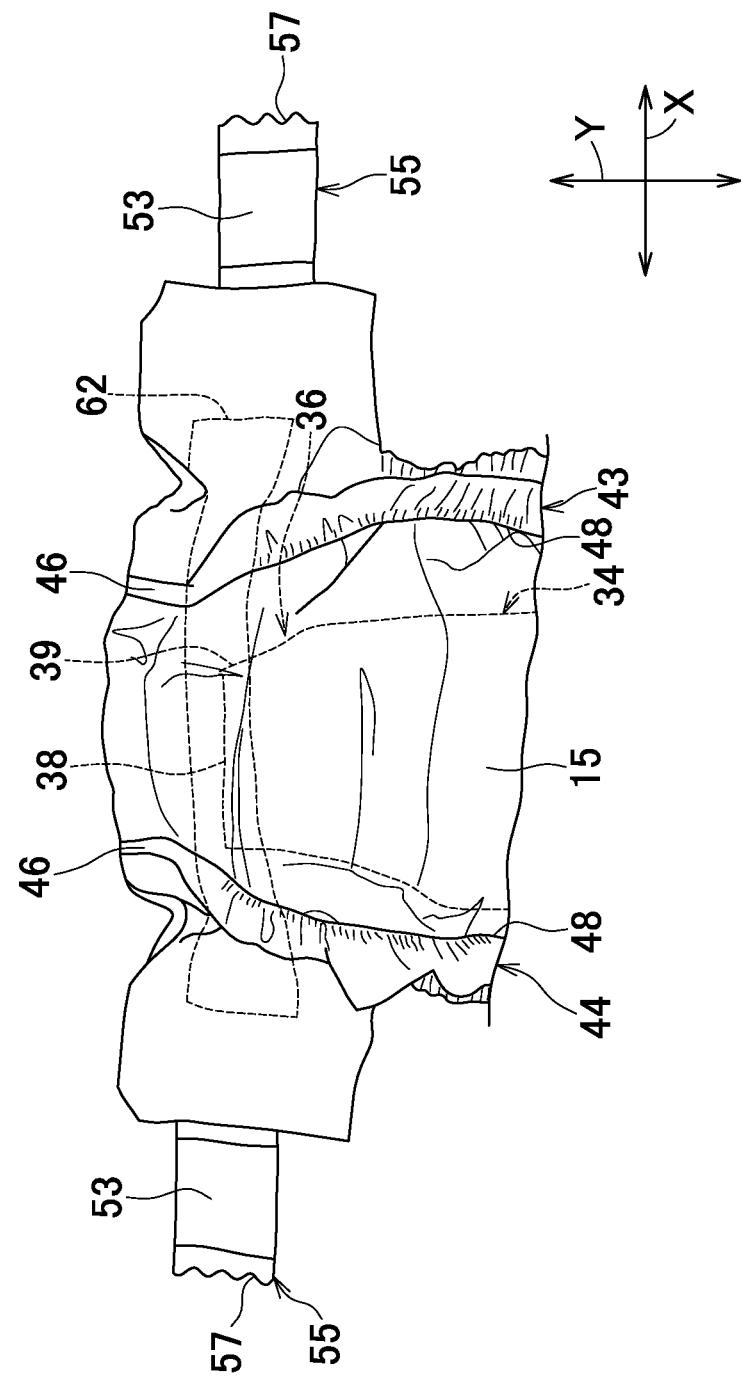
FIG. 14 is a plan view of a first end portion of an absorbent panel under contractile force of respective elastic members.

Referring to FIG. 11, the ventral side elastic member 62 has a belt-like shape of a predetermined dimension in the transverse direction X so that the ventral side elastic member 62 may overlap the first end 38 of the absorbent core 34 and a portion 39 of the absorbent core 34 having a dimension in the transverse direction X gradually narrows as the core 34 extends toward the transverse center line Q. Contraction of the ventral side elastic member 62 in the transverse direction X makes it possible to decrease a dimension in the transverse direction X of the first end 38 of the absorbent core 34 so that a dimension in the transverse direction X of the absorbent core 34 in its narrow region 36 may be gradually decreased from the side of the second end 40 toward the first end 38. In this way, it is possible to restrict a possibility that the absorbent core 34 might be indirectly caught by the both rear legs 7, thereby facilitating the diaper 10 to be put on the body of the pet animal 5. Furthermore, in the state of the ventral side elastic member 62 being held under tension, a dimension in the transverse direction X of the absorbent core 34 in the first end 38 may be set to be relatively large. In consequence, the functions and effects as have been described above may be assured without noticeably decreasing the absorbent capacity. In addition, it is possible to make the dimension in the transverse direction X of the absorbent core 34 as the ventral side elastic member 62 contracts in the transverse direction X, thereby enhancing the stiffness of the absorbent core 34 at the first end 38. In this way, the first end 38 of the absorbent core 34 to be passed between the both rear legs 7 of the pet animal 5 has the stiffness further enhanced and, for this reason, it is possible to put the diaper 10 on the body of the pet animal 5 further smoothly.

Contraction in the transverse direction X of the ventral side elastic member 62 decreases a dimension in the transverse direction X of the first end 38 and, in the ventral region 11, makes a central portion 63 in the transverse direction X including the longitudinal center line P project from the both lateral portions 26, 27 toward the side of the body-contact surface or toward the side of the non-body-contact surface. For example, as illustrated in FIG. 13 (b), in response to contraction of the ventral side elastic member 62 in the transverse direction X, in the ventral region 11, the central portion 63 in transverse direction X projects from the both lateral portions 26, 27 toward the side of the body-contact surface.

The state of the ventral region 11 in which the central portion 63 in the transverse direction X projects from the both lateral portions 26, 27 toward the side of the body-contact surface and the state of the ventral region 11 in which the central portion 63 in the transverse direction X projects from the both lateral portions 26, 27 toward the side of the non-body-contact surface may be converted each other. For example, in the state of the ventral region 11 in which the central portion 63 in the transverse direction X projects from the both lateral portions 26, 27 toward the side of the body-contact surface, the central portion 63 in the transverse direction X may be pushed with the finger from the side of the body-contact surface toward the side of the non-body-contact surface to convert the state to the state in which the central portion 63 in the transverse direction X projects from the both lateral portions 26, 27 toward the side of the non-body-contact surface.

Figure 15:
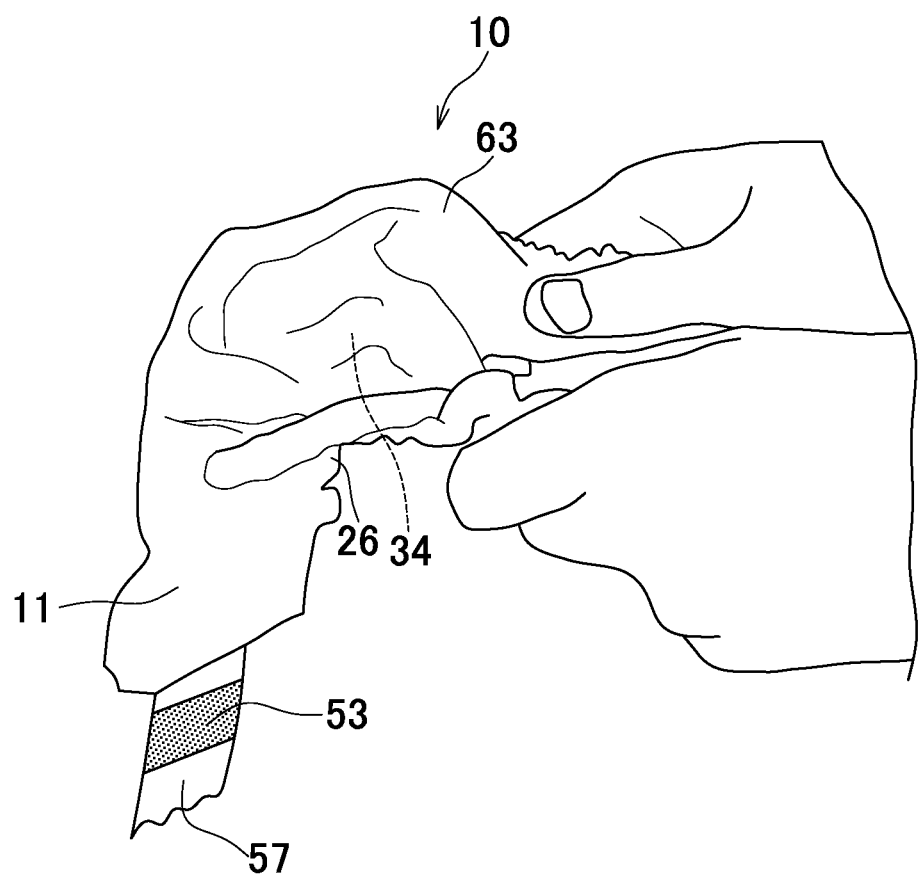
FIG. 15 is a perspective view illustrating a state in which the first end portion is gripped with a hand in the course of putting the diaper on the pet animal's body.

Referring to FIG. 13 (b) and FIG. 15, in the course of putting the diaper 10 on the body of the pet animal 5, the central portion 63 in the transverse direction X of the ventral region 11 may be projected from the both lateral portions 26, 27 toward the side of the body-contact surface to make the distal portions 57 of the pair of fastening tabs 55 hang down under an action of gravity, thereby setting apart the second fastening elements 53 from the skin of the pet animal 5. Whereby it is facilitated to pinch the second fastening elements 53 and to simplify handling of fastening the first and second fastening elements 52, 53 to each other.

Furthermore, in the course of putting the diaper 10 on the body of the pet animal 5, the central portion 63 in the transverse direction X of the ventral region 11 may be projected from the both lateral portions 26, 27 toward the side of the body-contact surface to put a central portion 34e in the transverse direction X of the absorbent core 34 in contact with the belly of the pet animal 5 and to put both lateral portions 34c, 34d in the transverse direction X of the absorbent core in contact with inguinal regions of the pet animal 5. In this way, the handling of putting the diaper 10 on the body of the pet animal 5 is further smooth.

An arrangement such that the one end of the containment-elastic member 49 in the ventral region 11 overlaps the ventral side elastic member 62 in the planar view makes it possible to project, in the ventral region 11, the central portion 63 in the transverse direction X from the both lateral portions 26, 27 toward the side of the body-contact surface or the side of the non-body-contact surface under mutual influence of contractile force between the two elastic members 49, 62. In the state of the central portion 63 in the transverse direction X projecting from the both lateral portions 26, 27 toward the side of the body-contact surface, it is possible to space the second fastening elements 53 from the skin of the pet animal and it is correspondingly made easy to pinch the second fastening elements 53 with the human fingers.

Furthermore, the arrangement such that, in the ventral region 11, one end of the lateral elastic member 29 overlaps the ventral side elastic member 62 in the planar view makes it possible to project the central portion 63 in the transverse direction X from the both lateral portions 26, 27 toward the side of the body-contact surface or toward the side of the non-body-contact surface. With the central portion 63 in the transverse direction X projects from the both lateral portions 26, 27 toward the side of the body-contact surface, it is possible to set the second fastening elements 53 apart from the skin of the pet animal and to make it easy to pinch the second fastening elements 53 with the human fingers. In this way, fastening between the first and second fastening elements 52, 53 is simplified.

According to this diaper 10, in addition to the functions and effects described hereinbefore, it is possible to restrict a decrease in the contractile force of the containment-elastic members 49 since there is no overlapping relationship between the proximal portions 45 of the containment sheet 43 and the absorbent core 34 and there is no overlapping relationship also between the front and rear ends 46, 47 of the containment sheet 43 and the absorbent core 34.

The ventral side elastic member 62 has been exemplarily described above to have the respective wide regions at the both ends in the transverse direction X and to have the constant width portion between the both ends. However, the present invention is not limited to such an arrangement but the ventral side elastic member may have, for example, a rectangular shape having a constant width in its entirety in the transverse direction X.

The disclosure relating to the present invention as described hereinabove may be arranged as follows:

The absorbent article for pet animals having a longitudinal direction, a transverse direction being orthogonal thereto, the body-contact surface facing pet animal's body and the non-body-contact surface lying on the side opposite thereto and including the absorbent panel having the ventral region, the dorsal region and the intermediate region defined between the ventral region and the dorsal region as viewed in the longitudinal direction wherein the absorbent panel includes the liquid-permeable interior sheet, the liquid-impermeable exterior sheet and the liquid absorbent core lying between these interior and exterior sheets. The liquid absorbent core is arranged in a limited area extending from a zone of the intermediate region defined adjacent to the slit for formation of an opening into which the pet animal's tail is inserted into the ventral region and has the first end lying in the ventral region and the second end lying in the intermediate region opposed to each other in the longitudinal direction; and the dimension in the transverse direction of the ventral region of the liquid absorbent core gradually narrows from the side of the second end toward the first end.

The present invention disclosed above may include at least embodiments as described below. These embodiments may be adopted in isolation or in combination with one another.

(1) The liquid absorbent core is divided into the narrow region having the first end and a wide region having the second end so that the liquid absorbent core may gradually narrow from the side of the second end toward the first end.

(2) In the liquid absorbent core, a dimension in the longitudinal direction of the narrow region is in a range of 30 to 90% of a dimension in the longitudinal direction of the liquid absorbent core.

(3) The absorbent article further includes the ventral side elastic member extending in the transverse direction in the ventral region wherein the ventral side elastic member is contractibly attached under tension between the liquid absorbent core and the exterior sheet and overlaps the first end of the liquid absorbent core in a planar view.

(4) The absorbent article further includes the pair of containment sheets extending in the longitudinal direction on the body-contact surface of the interior sheet wherein the pair of containment sheets have proximal portions secured to the interior sheet or the exterior sheet, the distal portions provided with the containment elastic members extending in the longitudinal direction and adapted to be set apart from the interior sheet under contraction of the containment elastic members and front and rear fixed ends secured to both ends in the longitudinal direction of the interior sheet so that the front and rear ends and the liquid absorbent core are not overlapped each other in a planar view.

(5) The absorbent article further including the fastener serving to fasten the ventral region and the dorsal region to each other wherein the fastener is disposed with the pair of fastening tabs extending outward in the transverse direction from both lateral portions of the ventral region; the fastening tabs respectively have distal portions secured to the interior sheet or the exterior sheet; and the first end of the liquid absorbent core partially extends outward in the longitudinal direction beyond end edges of the proximal portions lying on the side of the dorsal region.

(6) The respective ends of the containment elastic members overlap the ventral side elastic member in a planar view.

(7) The absorbent article further including the lateral elastic members extending in the longitudinal direction from the ventral region to the dorsal region and contractibly attached under tension between the containment sheets and the exterior sheet wherein ends of the lateral elastic members in the ventral region overlap the ventral side elastic member in a planar view.

REFERENCE SIGNS LIST

10 absorbent article for pet animal (diaper)
11 ventral region
12 dorsal region
13 intermediate region
15 topsheet (interior sheet)
16 backsheet (exterior sheet)
19 absorbent panel
20 fastener
22 slit for formation of opening
24 first end
25 second end
29 lateral elastic members
34 absorbent core
35 liquid-diffusive sheet
43 containment sheet
44 containment sheet
45 proximal portions
46 front end portion
47 rear end portion
48 distal portions
49 containment elastic members
52 first fastening element
53 second fastening elements
55 fastening tabs
62 ventral side elastic member
L1 dimension in transverse direction of absorbent core's first end
L2 dimension in transverse direction of absorbent core's second end L3 dimension in longitudinal direction of absorbent core's narrower region
L4 dimension in longitudinal direction of absorbent core
X transverse direction
Y longitudinal direction

The invention claimed is:

1. An absorbent article for pet animal, said absorbent article comprising:
   a longitudinal direction,
   a transverse direction being orthogonal to the longitudinal direction,
   a thickness direction being orthogonal to the longitudinal and transverse directions,
   a body-contact surface configured to face a pet animal's body,
   a non-body-contact surface opposite to the body-contact surface,
   an absorbent panel having a ventral region, a dorsal region and an intermediate region defined between the ventral region and the dorsal region in the longitudinal direction, and
   a ventral side elastic member extending in the transverse direction in the ventral region, wherein
   the absorbent panel includes
      a liquid-permeable interior sheet,
      a liquid-impermeable exterior sheet and
      a liquid absorbent core lying between the interior and exterior sheets,
   the liquid absorbent core is arranged in a limited area extending from a zone of the intermediate region into the ventral region, said zone of the intermediate region being adjacent to a slit defining an opening to receive the pet animal's tail,
   the liquid absorbent core is formed of a mixture of wood fluff pulp and absorbent polymer particles,
   the liquid absorbent core has
      a first end lying in the ventral region, and
      a second end lying in the intermediate region and opposing to the first end in the longitudinal direction,
   the liquid absorbent core includes a narrow region having the first end and a wide region having the second end,
   the narrow region of the liquid absorbent core has a portion overlapping the ventral side elastic member in the thickness direction, and gradually narrows from the first end toward the second end,
   a dimension of the first end in the transverse direction is less than a dimension of the second end in the transverse direction,
   the ventral side elastic member is contractibly attached under tension between the liquid absorbent core and the exterior sheet in the thickness direction, and
   the ventral side elastic member overlaps the first end of the liquid absorbent core in the thickness direction.

2. The absorbent article according to claim 1, wherein a dimension of the narrow region in the longitudinal direction is in a range of 30 to 90% of a dimension of the liquid absorbent core in the longitudinal direction.

3. The absorbent article according to claim 1, further comprising:
   a pair of containment sheets extending in the longitudinal direction on the interior sheet and configured to face the pet animal's body,
   wherein the pair of containment sheets have
   proximal portions secured to the interior sheet or the exterior sheet,
   distal portions disposed with containment elastic members extending in the longitudinal direction and adapted to be spaced apart from the interior sheet under contraction of the containment elastic members, and
   front and rear ends secured to both ends of the interior sheet in the longitudinal direction, wherein the front and rear ends do not overlap the liquid absorbent core in a planar view.

4. The absorbent article according to claim 3, further comprising:
   a fastener configured to fasten the ventral region and the dorsal region to each other, wherein
   the fastener comprises a pair of fastening tabs extending outward in the transverse direction from both lateral portions of the ventral region,
   the fastening tabs respectively have
      distal portions fixed to the interior sheet or the exterior sheet, and
      proximal portions opposing the distal portions in the transverse direction,
   the first end of the liquid absorbent core partially extends outward in the longitudinal direction beyond end edges of the proximal portions of the fastening tabs in the dorsal region.

5. The absorbent article according to claim 3, wherein respective ends of the containment elastic members overlap the ventral side elastic member in the planar view.

6. The absorbent article according to claim 3, further comprising:
   lateral elastic members extending in the longitudinal direction from the ventral region to the dorsal region and contractibly attached under tension between the containment sheets and the exterior sheet,
   wherein ends of the lateral elastic members in the ventral region overlap the ventral side elastic member in the planar view.

7. The absorbent article according to claim 1, wherein
   the first end of the liquid absorbent core is a most distal portion on one side of the liquid absorbent core in the longitudinal direction, and
   the second end of the liquid absorbent core is a most distal portion on the other side of the liquid absorbent core in the longitudinal direction.

* * * * *